United States Patent [19]
Honkanen et al.

[11] Patent Number: 5,948,902
[45] Date of Patent: Sep. 7, 1999

[54] ANTISENSE OLIGONUCLEOTIDES TO HUMAN SERINE/THREONINE PROTEIN PHOSPHATASE GENES

[75] Inventors: Richard E. Honkanen, Mobile, Ala.; Nicholas M. Dean, Encinitas, Calif.

[73] Assignees: South Alabama Medical Science Foundation, Mobile, Ala.; ISIS Pharmaceuticals, Inc., Carlsbad, Calif.

[21] Appl. No.: 08/975,211

[22] Filed: Nov. 20, 1997

[51] Int. Cl.$^6$ .............................. C07H 21/04; C12Q 1/68
[52] U.S. Cl. ................... 536/24.5; 536/23.1; 536/24.3; 536/24.31; 435/6; 435/91.1; 435/375
[58] Field of Search ............................ 435/6, 91.1, 440, 435/320.1, 366, 371, 375; 536/23.1, 23.5, 24.3, 24.31, 24.5

[56] References Cited

U.S. PATENT DOCUMENTS

| | | | |
|---|---|---|---|
| 5,034,506 | 7/1991 | Summerton et al. | 528/391 |
| 5,138,045 | 8/1992 | Cook et al. | 536/24.5 |
| 5,218,105 | 6/1993 | Cook et al. | 536/25.31 |
| 5,459,255 | 10/1995 | Cook et al. | 536/27.13 |
| 5,591,721 | 1/1997 | Agrawal et al. | 514/44 |

FOREIGN PATENT DOCUMENTS

WO 92/20823  11/1992  WIPO.

OTHER PUBLICATIONS

Zeng et al. Oncogene 12, 1557–1654 (1996).
Milligan et al. J. Of Medicinal Chemistry. 36, 1923–1937 (1993).
Cohen. Tibtech. 10, 87–91 (1992).
Chen et al. Embo Journal. 13 (18), 4278–4290 (1994).
Yong et al. Genomics. 29, 533–536 (1995).
Xu et al. Biochemical and Biophysical Research Communications. 218, 514–517 (1996).
Brewis et al. Biochemical et Biophysica ACTA. 1171, 231–233 (1992).
Norman et al. Mammalian Genome. 5, 41–45 (1994).
Barker et al. Biochimical et Biophysica ACTA. 1178 228–233 (1993).
Ammala et al., Proc Natl Acad Sci USA 91:4343–4347 (1994).
Ashihara et al., Methods in Enzymology LVIII: 248–262 (1979).
Berge et al., J Pharm Sci 66(1):1–19 (1977).
Cairns et al., J Biol Chem 269(12):9176–9183 (1994).
Chiang et al., J Biol Chem 266(27):18162–18171 (1991).
Cohen, TIBS 22:245–251 (1997).
Sanghvi, in Crooke, et al., Eds "Antisense Research and Applications", CRC Press, Boca Raton, pp. 276–278 (1993).
De Mesmaeker et al., Acc Chem Res 28:366–374 (1995).
Kabanov et al., FEBS Letters 259(2):327–330 (1990).
Kawasaki et al., J Med Chem 36:831–841 (1993).
Letsinger et al., Proc Natl Acad Sci USA 86:6553–6556 (1989).
Manoharan et al., Annals NY Acad Sci 660:306–309 (1992).
Manoharan et al., Nucleosides & Nucleotides 14(3–5):969–973 (1995).
Manoharan et al., Tetrahedron Letters 36(21):3651–3654 (1995).
Manoharan et al., Bioorganic & Med Chem Letters 4(8):1053–1060 (1994).
Manoharan et al., Bioorganic & Med Chem Letters 3(12):2765–2770 (1993).
Nielsen et al., Science 254:1497–1500 (1991).
Oberhauser et al., Nucl Acids Res 20(3):533–538 (1992).
Saison–Behmoaras et al., EMBO J 10(5):1111–1118 (1991).
Sambrook et al., "Molecular Cloning—A Laboratory Manual", Cold Spring Harbor Laboratory Press, Cold Spring Harbor 2:10.59–10.61 (1989).
Sambrook et al., "Molecular Cloning—A Laboratory Manual", Cold Spring Harbor Laboratory Press, Cold Spring Harbor 2:11.31–11.32 (1989).
Sanghvi et al., Nucl Acids Res 21(14):3197–3203 (1993).
Sogawa et al., Cancer Letters 89:1–6 (1995).
Sogawa et al., Res Comm Molec Path and Pharm 86(3):375–378 (1994).
Svinarchuk et al., Biochimie 75:49–54 (1993).
von Pierre Martin, Helv Chim Acta 78:486–504 (1995).
Wera et al., Biochem J 311:17–29 (1995).
Yamada et al., Res Comm Molec Path and Pharm 86(1):125–128 (1994).

*Primary Examiner*—John L. LeGuyader
*Assistant Examiner*—Mark L. Shibuya
*Attorney, Agent, or Firm*—Braman & Rogalskyj, LLP

[57] ABSTRACT

Oligonucleotides are provided which are targeted to nucleic acids encoding human serine/threonine protein phosphatases and which are capable of inhibiting protein phosphatase expression. Methods of inhibiting the expression of human protein serine/threonine phosphatases using oligonucleotides of the invention are also provided. The present invention further comprises methods of preventing or inhibiting hyperproliferation of cells and methods of treating abnormal conditions, including cancer, using oligonucleotides of the invention.

11 Claims, No Drawings

ANTISENSE OLIGONUCLEOTIDES TO HUMAN SERINE/THREONINE PROTEIN PHOSPHATASE GENES

This invention was made, in part, with Government support under grant NIH CA60750, awarded by the National Institutes of Health. The government may have certain rights in the invention.

FIELD OF THE INVENTION

This invention relates to compositions and methods for modulating expression of human serine/threonine protein phosphatases (PPs), naturally present cellular enzymes which have been implicated in abnormal cell proliferation, carcinogenesis and tumor formation. Compositions and methods for specifically modulating the expression of serine/threonine protein phosphatase 1γ1 (PP1γ1), serine/threonine protein phosphatase 4 (PP4) and serine/threonine protein phosphatase 5 (PP5) are provided. This invention is also directed to methods for inhibiting hyperproliferation of cells; these methods can be used diagnostically or therapeutically. Furthermore, this invention is directed to treatment of conditions, particularly hyperproliferative conditions such as cancer, which are associated with expression of human serine/threonine protein phosphatases.

BACKGROUND OF THE INVENTION

Throughout this application various publications are referenced. The disclosures of each of these publications in their entireties are hereby incorporated by reference in this application.

The reversible phosphorylation of proteins on serine and threonine residues is a major intracellular control mechanism. Cell proliferation, cell signaling, gene expression and mitosis are among the cellular functions regulated by this mechanism. The phosphorylation state of a protein is controlled by kinases, which phosphorylate proteins, and phosphatases, which dephosphorylate proteins. A number of families and types of protein phosphatases exist, including tyrosine phosphatases and serine/threonine protein phosphatases (PPs). An increase in expression of certain PPs has been described in several tumor types. Modulation of expression of one or more serine/threonine protein phosphatases is desired for research, diagnostic, and therapeutic uses.

Small molecule inhibitors of protein phosphatases have been used to study PP function. The best characterized of these is okadaic acid, which is the causative agent of diarrhetic shellfish poisoning. It is a potent inhibitor of PP2A and PP1 and a much (roughly a thousandfold) less potent inhibitor of PP2B. In spite of this difference in sensitivity, okadaic acid cannot easily be used to discriminate between PP1 and PP2A in cells. Other inhibitors of one or more PPs include tautomycin, cyclosporin A, dinophysistoxin, calyculin, microcystin, nodularin and cantharidin. Cairns et al., 1994, J. Biol. Chem. 269:9176–9183; Wera and Hemmings, 1995, Biochem. J. 311:17–29.

Improved inhibitors of protein phosphatases are desired for therapeutic, diagnostic and research uses. Specific inhibitors of particular PP isoforms are particularly desired.

Oligonucleotides have been employed as therapeutic moieties in the treatment of disease states in animals and man. For example, workers in the field have now identified antisense, triplex and other oligonucleotide compositions which are capable of modulating expression of genes implicated in viral, fungal and metabolic diseases.

Antisense oligonucleotides have been safely administered to humans and clinical trials of several antisense oligonucleotide drugs, targeted both to viral and cellular gene products, are presently underway. For example, the oligonucleotide drug fomivirsen (ISIS 2922), has been shown to be effective against cytomegalovirus retinitis in AIDS patients, and is presently in Phase III clinical trials. BioWorld Today, Apr. 29, 1994, p 3. Another oligonucleotide drug, ISIS 2302, has been shown to be effective in Crohn's disease, a form of inflammatory bowel disease. In a placebo-controlled Phase II trial of ISIS 2302 in Crohn's disease, a statistically significant (p=0.0001) corticosteroid-sparing effect was achieved while inducing durable remissions in almost half of the drug-treated patients (versus 0% in the placebo group). The mean duration of remission in the responding patients was prolonged, lasting almost five months following a single course of treatment. In addition, ISIS 2302 was shown to be safe and well-tolerated. Canadian Digestive Diseases Week conference in Quebec City, Quebec, Canada.

It is thus established that oligonucleotides can be useful therapeutic instrumentalities and can be useful in treatment of cells and animal subjects, especially humans.

SUMMARY OF THE INVENTION

The present invention provides oligonucleotides which are targeted to nucleic acids encoding human serine/threonine protein phosphatases, particularly PP1γ1, PP4 and PP5, and which are capable of inhibiting PP expression. The oligonucleotides of the invention are believed to be useful both diagnostically and therapeutically, and are believed to be particularly useful in the methods of the present invention. The oligonucleotides are also believed to be useful as research reagents.

The present invention also comprises methods of inhibiting the expression of human PP. These methods are believed to be useful both therapeutically and diagnostically as a consequence of the association between PP expression and hyperproliferation, particularly certain tumor types described hereinabove. These methods are also useful as tools, for example for detecting and determining the role of PP expression in various cell functions and physiological processes and conditions and for diagnosing conditions associated with PP expression. The methods provided are particularly useful for distinguishing between particular PP isoforms.

The present invention also comprises methods of inhibiting hyperproliferation of cells using oligonucleotides of the invention. These methods are believed to be useful in diagnosis, prevention and treatment of PP-associated cell hyperproliferation. These methods employ the oligonucleotides of the invention.

DETAILED DESCRIPTION OF THE INVENTION

The reversible phosphorylation of proteins on serine and threonine residues is a major intracellular control mechanism. Cell proliferation, cell signaling, gene expression and mitosis are among the cellular functions regulated by this mechanism. The phosphorylation state of a protein is controlled by kinases, which phosphorylate proteins, and phosphatases, which dephosphorylate proteins. A number of families and types of protein phosphatases exist, including tyrosine phosphatases and serine/threonine protein phosphatases (PPs). Antisense inhibitors of serine/threonine PPs are the subject of the present invention. Various types and isoforms of PPs have been described. These include PP1

(including α, β, γ1, γ2 and δ isoforms) PP2A(including α and β), PP2B (including α, β and γ) (also called calcineurin-CNA, CMP), PP2C, PP4 (also called PPX), PP5 and PP6 (also called PPV and sit-4). For a review of serine/threonine phosphatases and their nomenclature, see Cohen, P. T. W. (1997) Trends in Biol. Sci., 22:245–251. A selective increase in expression of PP1α and PP1γ1 has been described in liposarcoma and of PP1γ1 in osteogenic tumors (chondrosarcoma and osteosarcoma)and malignant fibrous histiocytoma, and some isoform of PP1 is believed to be involved in carcinogenesis. Sogawa et al. (1995) Cancer Letters 89:1–6; Sogawa et al., 1994, Res. Comm. in Mol. Pathol. and Pharmacol. 86:375–378; Yamada et al. (1994) Res. Comm. in Mol. Pathol. and Pharmacol. 86:125–128.

Certain abnormal proliferative or hyperproliferative conditions are believed to be associated with PP expression and are, therefore, believed to be responsive to inhibition of PP expression. Abnormally high levels of expression of the PP protein are implicated in carcinogenesis, i.e., the development of abnormal proliferative or hyperproliferative conditions. These abnormal conditions are also believed to be responsive to inhibition of PP expression. Examples of abnormal proliferative conditions are hyperproliferative disorders such as cancers, tumors and hyperplasias, including smooth muscle cell proliferation in the blood vessels, such as stenosis or restenosis following angioplasty. It is believed that elimination or reduction of PP expression may halt or reverse abnormal cell proliferation. This is believed to be true even when levels of PP expression are not abnormally high.

There is a great desire to provide compositions of matter which can modulate the expression of PPs. It is also desired to provide methods of detection of nucleic acids encoding PPs in cells, tissues and animals. It is also desired to provide methods of diagnosis and treatment of conditions associated with abnormal PP expression. In addition, kits and reagents for detection and study of nucleic acids encoding PP are desired. "Abnormal" PP expression is defined herein as abnormally high levels of expression of the PP protein, expression of an abnormal or mutant PP protein, or any level of PP expression associated with an abnormal condition or state.

The present invention employs oligonucleotides targeted to nucleic acids encoding serine/threonine protein phosphatases. The relationship between an oligonucleotide and its complementary nucleic acid target to which it hybridizes is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding a protein phosphatase; in other words, a protein phosphatase gene or mRNA expressed from a protein phosphatase gene. The targeting process also includes determination of a site or sites within the nucleic acid sequence for the oligonucleotide interaction to occur such that the desired effect—modulation of gene expression—will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of protein phosphatase gene expression is presently the preferred form of modulation. This modulation can be measured in ways which are routine in the art, for example by Northern blot assay of mRNA expression or Western blot assay of protein expression as taught in the examples of the instant application. Effects on cell proliferation can also be measured, as taught in the examples of the instant application. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid nonspecific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

In preferred embodiments of this invention, oligonucleotides are provided which are targeted to mRNA encoding serine/threonine protein phosphatase 1γ1 (PP1γ1), serine/threonine protein phosphatase 4 (PP4) and serine/threonine protein phosphatase 5 (PP5). In accordance with this invention, persons of ordinary skill in the art will understand that mRNA includes not only the coding region which carries the information to encode a protein using the three letter genetic code, including the translation start and stop codons, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. In preferred embodiments, the oligonucleotide is targeted to a translation initiation site (AUG codon) or sequences in the coding region, 5' untranslated region or 3'-untranslated region of mRNA encoding human PP1γ1, PP4 and PP5. The functions of mRNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with PP expression.

The present invention provides oligonucleotides for modulation of PP gene expression. Such oligonucleotides are targeted to nucleic acids encoding PPs. Oligonucleotides and methods for modulation of PP1γ1, PP4 and PP5 are provided; however, compositions and methods for modulating expression of other forms of serine/threonine protein phosphatases are also believed to have utility and are comprehended by this invention. As hereinbefore defined, "modulation" means either inhibition or stimulation. Inhibition of PP gene expression is presently the preferred form of modulation.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Certain preferred oligonucleotides of this invention are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Consequently, comparable results can often be obtained with shorter oligonucleotides when chimeric oligos are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one preferred embodiment, a chimeric oligonucleotide comprises at least one region modified to increase target binding affinity, and, usually, a region that acts as a substrate for RNAse H. Affinity of an oligonucleotide for its target (in this case a nucleic acid encoding a protein phosphatase) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In a more preferred embodiment, the region of the oligonucleotide which is modified to increase PP mRNA binding affinity comprises at least one nucleotide modified at the 2' position of the sugar, most preferably a 2'-O-alkyl, 2'-O-alkyl-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of PP gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. oligonucleotides which contain at least one phosphorothioate modification are presently more preferred. In some cases, oligonucleotide modifications which enhance target binding affinity are also, independently, able to enhance nuclease resistance. A discussion of antisense oligonucleotides and some desirable modifications can be found in De Mesmaeker et al., 1995, Acc. Chem. Res. 28:366–374.

Specific examples of some preferred oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, $CH_2$—$N(CH_3)$—O—$CH_2$ [known as a methylene (methylimino) or MMI backbone], $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones, wherein the native phosphodiester backbone is represented as O—P—O—$CH_2$). The amide backbones disclosed by De Mesmaeker et al. (1995, Acc. Chem. Res. 28:366–374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., Science, 1991, 254, 1497). Oligonucleotides may also contain one or more substituted sugar moieties. Preferred oligonucleotides comprise one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy (also known in the art as O-alkyl-O-alkyl), substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O-$CH_2CH_2OCH_3$, also known as 2'-O-(2-methoxyethyl) or 2'-MOE] (Martin et al., Helv. Chim. Acta, 1995, 78, 486). Other preferred modifications include 2'-methoxy (2'-O-$CH_3$), 2'-propoxy (2'-O$CH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2' deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-thiouracil, 2thiothymine, 5-bromouracil, 5-hydroxymethyluracil, 8-azaguanine, 7-deazaguanine, $N^6$(6-aminohexyl) adenine and 2,6-diaminopurine. Kornberg, A., DNA Replication, W.H. Freeman & Co., San Francisco, 1980, pp 75–77; Gebeyehu, G., et al., 1987, Nucl. Acids Res. 15:4513). A "universal" base known in the art, e.g., inosine, may be included. 5-me-C substitutions have been shown to increase nucleic acid duplex stability by 0.6–1.2° C. (Sanghvi, Y. S., in Crooke, S. T. and Lebleu, B., eds., Antisense Research and Applications, CRC Press, Boca Raton, 1993, pp. 276–278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., Proc. Natl. Acad. Sci. USA, 1989, 86, 6553), cholic acid (Manoharan et al., Bioorg. Med. Chem. Let., 1994, 4, 1053), a thioether, e.g., hexyl-S-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651). Oligonucleotides comprising lipophilic moieties, and methods for preparing such oligonucleotides are known in the art, for example, U.S. Pat. No. 5,138,045, U.S. Pat. No. 5,218,105 and U.S. Pat. No. 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes chimeric oligonucleotides as hereinbefore defined.

The compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the oligonucleotides of the invention, pharmaceutically acceptable salts of such prodrugs, and other bioequivalents.

Prodrugs: The oligonucleotides of the invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

Pharmaceutically Acceptable Salts: The term pharmaceutically acceptable salts refers to physiologically and pharmaceutically acceptable salts of the oligonucleotides of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides in accordance with this invention preferably are from about 8 to about 50 nucleotides in length. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

It has now been found that certain oligonucleotides targeted to portions of PP1γ1, PP4 and PP5 mRNA are useful for inhibiting PP expression. Inhibition of PP expression using antisense oligonucleotides is believed to be useful for interfering with cell hyperproliferation. In the methods of the invention, tissues or cells are contacted with oligonucleotides. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

For therapeutics, methods of inhibiting hyperproliferation of cells and methods of preventing and treating abnormal proliferative conditions are provided. The formulation of therapeutic compositions and their subsequent administration is believed to be within the skill in the art. In general, for therapeutics, a patient suspected of needing such therapy is given an oligonucleotide in accordance with the invention, commonly in a pharmaceutically acceptable carrier, in amounts and for periods which will vary depending upon the nature of the particular disease, its severity and the patient's overall condition. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip or infusion, subcutaneous, intraperitoneal or intramuscular injection, pulmonary administration, e.g., by inhalation or insufflation, or intrathecal or intraventricular administration. For oral administration, it has been found that oligonucleotides with at least one 2'-substituted ribonucleotide are particularly useful because of their absortion and distribution characteristics. U.S. Pat. No. 5,591,721 (Agrawal et al.). Oligonucleotides with at least one 2'-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral, intrathecal or intraventricular administration may include sterile aqueous solutions which may also contain buffers, diluents and other suitable additives.

In addition to such pharmaceutical carriers, cationic lipids may be included in the formulation to facilitate oligonucleotide uptake. One such composition shown to facilitate uptake is Lipofectin (BRL, Bethesda MD).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be calculated based on $IC_{50}$'s or $EC_{50}$'s in in vitro and in vivo animal studies. For example, given the molecular weight of compound (derived from oligonucleotide sequence and chemical structure) and an effective dose such as an $IC_{50}$, for example (derived experimentally), a dose in mg/kg is routinely calculated.

The present invention is also suitable for diagnosing abnormal proliferative states in tissue or other samples from patients suspected of having a hyperproliferative disease such as cancer. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. Similarly, the present invention can be used to distinguish PP-associated, or, particularly, PP1γ1, PP4 or PP5-associated tumors from tumors having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

The oligonucleotides of the invention are also useful for detection and diagnosis of PP expression. For example, radiolabeled oligonucleotides can be prepared by $^{32}P$ labeling at the 5' end with polynucleotide kinase. Sambrook et al.,

*Molecular Cloning. A Laboratory Manual,* Cold Spring Harbor Laboratory Press, 1989, Volume 2, p. 10.59. Radiolabeled oligonucleotides are then contacted with tissue or cell samples suspected of PP expression and the sample is washed to remove unbound oligonucleotide. Radioactivity remaining in the sample indicates bound oligonucleotide (which in turn indicates the presence of PP) and can be quantitated using a scintillation counter or other routine means. Radiolabeled oligo can also be used to perform autoradiography of tissues to determine the localization, distribution and quantitation of PP expression for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing PP. Quantitation of the silver grains permits P expression to be detected.

Analogous assays for fluorescent detection of PP expression can be developed using oligonucleotides of the invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling Va. See 1993 Catalog of Products for DNA Research, Glen Research, Sterling Va., p. 21).

Each of these assay formats is known in the art. One of skill could easily adapt these known assays for detection of PP expression in accordance with the teachings of the invention providing a novel and useful means to detect PP expression.

Oligonucleotide inhibition of PP5 expression

The oligonucleotides shown in Table 1 were designed using the Genbank sequences HSSERTHRP (Genbank accession number X92121), HSRNAPPP5 (Genbank accession number X89416) and PPP5C (Genbank accession number U25174), synthesized and tested for inhibition of PP5 mRNA expression in A549 cells using a Northern blot assay. All oligonucleotides shown in Table 1 are chimeric oligonucleotides with central 2'-deoxy "gaps," which have phosphorothioate backbones, flanked on both sides by 2'-methoxyethoxy (2'-MOE) "wings" (shown in bold), which have phosphodiester backbones. All cytosines in the 2'-MOE wings are 5-methylcytosines.

In the initial screen, A549 cells were treated with oligonucleotides at a concentration of 300 nM oligonucleotide for four hours in the presence of 20 mg/ml lipofectin. Results were normalized and expressed as a percent of control. The effect of each oligonucleotide on levels of PP5 mRNA, expressed as approximate percent inhibition compared to control, is shown in Table 1. In this initial screen, oligonucleotides giving a reduction of PP5 mRNA of approximately 50% or greater were considered active. According to this criterion, oligonucleotides 14493, 14494, 14495, 14496, 14498, 14499 and 14504 were found to be active. These sequences (SEQ ID NO: 1, 2, 3, 4, 6, 7 and 12, respectively, SEQ ID Nos shown in bold in Table 1) are therefore preferred. Of these, oligonucleotides 14493, 14498 and 14504 (SEQ ID NO: 1, 6 and 12, respectively) showed at least 70% inhibition of PP5 mRNA in this assay and are highly active.

Additional oligonucleotides targeted to PP5:

Additional oligonucleotides targeted to PP5 and having SEQ ID NO: 12 were synthesized. These are chimeric oligonucleotides having slightly wider deoxy gaps (and shorter 2'-MOE wings, shown in bold) than ISIS 14504. These oligonucleotides are shown in Table 2, along with ISIS 15521, a mismatch control.

These oligonucleotides differ in their backbone composition; ISIS 15523 is uniformly phosphorothioate (P=S) and ISIS 15534 is a mixed backbone compound with a phosphodiester backbone (P=O) in the wings and phosphorothioate (P=S) in the deoxy gap. ISIS 15521, the mismatch control, is also a mixed backbone compound with phosphodiester wings and a phosphorothiate gap.

These oligonucleotides were tested for their ability to reduce PP5 mRNA levels in A549 cells, using oligonucleotide doses of 25 to 500 nM. ISIS 15523 demonstrated an $IC_{50}$ of approximately 100 nM, and ISIS 15534 demonstrated an $IC_{50}$ of approximately 135 nM. The mismatch control, ISIS 15521, did not inhibit PP5 mRNA levels by more than 20% at any of the doses tested.

Effect of antisense inhibition of PP5 expression on cell proliferation:

A549 cells were treated with ISIS nb or its scrambled control, ISIS 15521 at a concentration of 300 nM. Each day for the next 5 days, viable cells were counted. The scrambled control oligonucleotide, ISIS 11521, was approximately equivalent to untreated control on all 5 days. In contrast, the cells treated with ISIS 15534 showed markedly decreased proliferation compared to untreated cells. On days 2, 3, 4 and 5, ISIS 15534-treated cells showed a decrease in proliferation of 55%, 75%, 89% and 55%, respectively, compared to control.

Effect of antisense inhibition of PP5 expression on DNA replication:

A549 cells were treated with ISIS 15534 or its scrambled control, ISIS 15521 at a concentration of 300 nM. Cells were pulse-labeled with [$^3$H] -thymidine for 5 hours at intervals over the next five days. Cells were lysed and [$^3$H]-thymidine incorporation (indicative of DNA synthesis) was determined by liquid scintillation counting. The scrambled control oligonucleotide, ISIS 11521, was approximately equivalent to untreated control on all 5 days. In contrast, the cells treated with ISIS 15534 showed markedly decreased thymidine incorporation compared to untreated cells. On days 2, 3, 4 and 5, ISIS 15534-treated cells showed a decrease in [$^3$H]-thymidine incorporation of approximately 85%, 88% and 62%, respectively, compared to control. By day 5 [$^3$H]-thymidine incorporation was approximately equivalent in treated and untreated cells.

Additional oligonucleotides targeted to PP5:

An additional oligonucleotides targeted to PP5 and having SEQ ID NO: 1 was synthesized. This compound, ISIS 15516 has a phosphorothioate backbone and is a chimeric oligonucleotide having a slightly wider deoxy gap (and shorter 2'-MOE wings, shown in bold) than ISIS 14493. These oligonucleotides are shown in Table 3, along with ISIS 15517, a mismatch control with a mixed backbone (P=S in the gap, P=O in the wings).

ISIS 15516 and 15517 oligonucleotides were tested for their ability to reduce PP5 mRNA levels in RINm5f cells. Dose response curves were generated for oligonucleotide doses of 25 to 500 nM. ISIS 15516 demonstrated an $IC_{50}$ of approximately 135 nM. The scrambled control, ISIS 15517, gave less than 10% reduction of PP5 mRNA levels at any dose tested.

RINm5f cells are an insulin-secreting insulinoma rat cell line. Previous studies indicate that there is a correlation between cell growth, insulin secretion, calcium channel activity and phosphatases in RINm5f cells. In both humans and rat, calcium channels are phosphorylated, and phosphorylation is believed to keep the channel closed (i.e., phosphorylation causes a decrease in the frequency and/or duration of channel opening). There is substantial evidence that calcium channels are involved in the regulation of insulin secretion. Calcium channel blockers such as nifedipine and verapamil are used in the treatment of cardiac disorders, such as angina, congestive heart failure and certain arrhythmias, as well as hypertension. Thus agents that affect calcium channels, particularly calcium channel blockers, are believed to be therapeutically useful.

The antisense oligonucleotide ISIS 15516 (SEQ ID NO: 1), targeted to the AUG region of human PP5, was tested in RINm5f cells for its effect on calcium channels, using standard patch-clamp techniques. Because the human and rat PP5 mRNA sequences are identical in the target region of this oligonucleotide, ISIS 15516 is perfectly complementary to this portion of the rat PP5 sequence. Treatment of RINm5f cells with a 300 nM concentration of ISIS 15516 indicated that this compound decreases calcium currents in these cells. The mismatch control oligonucleotide, ISIS 15517, did not show this effect. Since inhibition of PP5 expression by ISIS 15516 is now shown to decrease calcium current density, it is believed that this compound and other inhibitors of PP5 may be useful as calcium channel blockers, for example in treatment of cardiac conditions.

Oligonucleotide inhibition of PP4 expression

The oligonucleotides shown in Table 4, targeted to human PP4 (also known as protein phosphatase X) were designed using the Genbank sequence HSPPX (Genbank accession number X70218), synthesized and tested for inhibition of PP4 mRNA expression in A549 cells using a Northern blot assay. All oligonucleotides shown in Table 4 are chimeric oligonucleotides with central 2'-deoxy "gaps," which have phosphorothioate backbones, flanked on both sides by 2'-methoxyethoxy (2'-MOE) "wings" (shown in bold), which have phosphodiester backbones. All cytosines in the 2'-MOE wings are 5-methylcytosines.

In this initial screen, oligonucleotides giving a reduction of PP4 mRNA of approximately 50% or greater were considered active. According to this criterion, oligonucleotides 14375, 14376, 14378, 14379, 14380, 14383, 14385 and 14387 were found to be active. These sequences (SEQ ID NO: 16, 17, 19, 20, 21, 23, 24 and 25, respectively, SEQ ID NOs shown in bold in Table 4) are therefore preferred. Of these, oligonucleotides 14375, 14376, 14379 and 14387 (SEQ ID NO: 16, 17, 20, and 25, respectively) showed at least 70% inhibition of PP1γ1 mRNA in this assay and are highly active.

Oligonucleotide inhibition of PP1 expression

The oligonucleotides shown in Table 5, targeted to human PP1γ1 were designed using the Genbank sequence HSP-PICC (Genbank accession number X74008), synthesized and tested for inhibition of PP1γ1 mRNA expression in A549 cells using a Northern blot assay. All oligonucleotides shown in Table 5 are chimeric oligonucleotides with central 2'-deoxy "gaps," which have phosphorothioate backbones, flanked on both sides by 2'-methoxyethoxy (2'-MOE) "wings" (shown in bold), which have phosphodiester backbones. All cytosines in the 2'-MOE wings are 5-methylcytosines. Oligonucleotides were tested at a concentration of 300 nM and results are shown (as percent inhibition compared to control) in Table 5.

In this initial screen, oligonucleotides giving a reduction of PP1γ1 mRNA of approximately 50% or greater were considered active. According to this criterion, oligonucleotides 14435, 14436, 14439 and 14441 were found to be active. These sequences (SEQ ID NO: 31, 32, 35 and 37, respectively, SEQ ID NOs shown in bold in Table 5) are therefore preferred. Of these, oligonucleotides 14435 and 14436 (SEQ ID NO: 31 and 32, respectively) showed at least 70% inhibition of PP1γ1 mRNA in this assay and are highly active.

Dose response curves were obtained for several PP1γ1 oligonucleotides, from which $IC_{50}$s were calculated. ISIS 14439 demonstrated an $IC_{50}$ of less than 50 nM. ISIS 14441 demonstrated an $IC_{50}$ of approximately 125 nM. ISIS 14436 showed an $IC_{50}$ of approximately 150 nM and ISIS 14435 showed an $IC_{50}$ of approximately 180 nM. ISIS 15032, an analog of ISIS 14435 with a uniformly phosphorothioate backbone and 2' MOE wings flanking a 10-nucleotide deoxy gap, demonstrated an estimated $IC_{50}$ of between 50 and 100 nM.

Specificity of oligonucleotides for PP isoforms:

Several oligonucleotides which were determined to be active against their particular target protein phosphatase isoform were tested to see if they had any effects on other isoforms. None of the PP1γ1 oligonucleotides tested (14430, 14431, 14432, 14433, 14434 and 14435) had any effect on PP2Aα mRNA levels. ISIS 14441 was also tested for ability to inhibit PP5 and had no effect. ISIS 14439, another oligonucleotide targeted to PP1γ1, had no effects on the other PP1 isoforms, PP1α and PP1β. ISIS 15032, the uniformly P=S analog of 14435, also had no inhibitory effect on PP1α or PP1β mRNA levels.

EXAMPLES

Example 1

Synthesis and Characterization of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites are purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides were synthesized using 2'-methoxy β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides were synthesized as described in Kawasaki et al., J. Med. Chem. 1993, 36, 831–841. Briefly, the protected nucleoside $N^6$-benzoyl-2'-deoxy-2'-fluoroadenosine was synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-β-D-arabinofuranosyladenine was selectively protected in moderate yield as the 3',5'-ditetrahydropyranyl (THP) intermediate. Deprotection of the THP and $N^6$-benzoyl groups was accomplished using standard methodologies and standard methods were used to obtain the 5'-dimethoxytrityl- (DMT) and 5'-DMT-3'-phosphoramidite intermediates.

The synthesis of 2'-deoxy-2'-fluoroguanosine was accomplished using tetraisopropyldisiloxanyl (TPDS) protected 9-β-D-arabinofuranosylguanine as starting material, and conversion to the intermediate diisobutyrylarabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT-and 5'-DMT-3'-phosphoramidites.

Synthesis of 2'-deoxy-2'-fluorouridine was accomplished by the modification of a literature procedure in which 2,2'-anhydro-1-β-D-arabinofuranosyluracil was treated with 70% hydrogen fluoride-pyridine. Standard procedures were used to obtain the 5'-DMT and 5'-DMT-3'-phosphoramidites.

2'-deoxy-2'-fluorocytidine was synthesized via amination of 2'-deoxy-2'-fluorouridine, followed by selective protection to give $N^4$-benzoyl-2'-deoxy-2'-fluorocytidine. Standard procedures were used to obtain the 5'-DMT and 5'-DMT-3' phosphoramidites.

2'-(2-methoxyethyl)-modified amidites are synthesized according to Martin, P., Helv. Chim. Acta 1995, 78,486–504. For ease of synthesis, the last nucleotide was a deoxynucleotide. 2'-O-$CH_2CH_2OCH_3$ cytosines may be 5-methyl cytosines.

Synthesis of 5-Methyl cytosine monomers:

2,2'-Anhydro[1-β-D-arabinofuranosyl)-5-methyluridine]:

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine:

2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine:

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine:

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine:

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine:

A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

$N^4$-Benzoyl-2'-O-methoxyethyl-5'-O-dimethoxytrityl-5-methylcytidine:

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

$N^4$-Benzoyl-2'-O-methoxyethyl-5'-O-dimethoxytrityl-5methylcytidine-3'-amidite:

$N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods (Sanghvi et al., 1993, Nucl. Acids Res. 21:3197–3203) using commercially available phosphoramidites (Glen Research, Sterling Va. or ChemGenes, Needham Mass.).

Oligonucleotides having methylene(methylimino) backbones are synthesized according to U.S. Pat. No. 5,378,825, which is coassigned to the assignee of the present invention and is incorporated herein in its entirety. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al., Acc. Chem. Res. 1995, 28, 366–374. The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P.E. Nielsen et al., Science 1991, 254, 1497).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}P$ nuclear magnetic resonance spectroscopy, and for some studies oligonucleotides were purified by HPLC, as described by Chiang et al., 1991, J. Biol. Chem., 266:18162–18171. Results obtained with HPLC-purified material were similar to those obtained with non-HPLC purified material.

Example 2

Northern blot analysis of inhibition of protein phosphatase mRNA expression

The human lung tumor cell line A549 was obtained from the American Type Culture Collection (Rockville Md.) and were grown in DMEM (Gibco BRL, Gaithersburg Md.), supplemented with 10% fetal calf. Cells were seeded on 60 mm plates. When they reached 70% confluency, they were washed with DMEM and 1 ml of DMEM containing 15 µg/ml DOTMA/DOPE (Lipofectin®, GIBCO-BRL) and oligonucleotide at desired concentration was added. Duplicate dishes were used for each treatment condition. After 4 hours of treatment at 37°, cells were washed and cultured in fresh DMEM containing 10% fetal bovine serum for an additional 17 hours. Cells were then harvested and total RNA was extracted with TRIzol Reagent (GIBCO-BRL) according to manufacturer's protocol. Total RNA (20 µg) was fractionated on a 1% agarose gel containing formaldehyde, and transferred to a DURLON-UV (Stratagene) nylon membrane. Following UV crosslinking, the filters were hybridized with the appropriate protein phosphatase probe. The $^{32}P$-labeled human PP cDNA probes are generated with DECAPrime® DNA Labeling Kit (Ambion) according to the manufacturer's protocol. Hybridization was performed in a hybridization solution containing 50% formamide at 42° for 16 hours. This was followed by two low stringency washes (2×SSC) at room temperature and two high stringency washes (0.1×SSC/0.5% SDS) at 55° C. Hybridization signals were visualized by autoradiography, and filters were then stripped and reprobed with a $^{32}P$-labeled glyceraldehyde-3-phosphate dehydrogenase (GAPDH) probe to confirm equal loading. The densities of hybridization signals were measured with the NIH Image program (ImagePC).

Example 3

Antisense inhibition of cell proliferation

A549 cells were seeded in 12-well tissue culture plates at about 50% confluence in DMEM containing 10% fetal bovine serum. The next day, cells were treated with the PP5-specific antisense oligonucleotide, ISIS 15534, or its scrambled control, ISIS 15521, at a final concentration of 300 nM as described in Example 2. On each of the following 5 days, cultures from three wells of each treatment gruop were trypsinized, collected and counted. Cell viability was determined by trypan blue staining, and the results given are the mean of three independent experiments.

Example 4

Measurement of [$^3$H]-thymine incorporation

A 549 cells were subcultured in 24-well tissue culture plates and treated with the PP5-specific antisense oligonucleotide ISIS 15534 or its scrambled control, ISIS 15521 at a final concentration of 300 nM as described in Example 2. At timed intervals during the next 5 days, cells were pulse-labeled with [$^3$H]-thymidine (0.5 µCi/ml) for 5 hours. The cells were then lysed, and [$^3$H]-thymidine incorporation was determined by liquid scintillation counting using standard methods (Baserga, R. and Ashihara, T., (1979) Methods in Enzymology LVIII:248–262). The results given are the mean of three independent experiments.

Example 5

Effect of oligonucleotides on calcium channels

The effect of antisense oligonucleotides on calcium channels was tested in RINm5f cells. This is an insulin-secreting insulinoma rat cell line available from the American Type Culture Collection, Rockville Md. Calcium currents were measured using standard patch-clamp techniques to measure ion conductance. These techniques are described in, for example, Ammala et al., 1994, Proc. Natl. Acad. Sci., USA, 91:4343–4347.

Example 6

A549 xenografts

A549 cells are obtained from the American Type Culture Collection (Bethesda Md.) and grown in T-75 flasks until 65–75% confluent. $5 \times 10^6$ A549 cells are implanted subcutaneously in the inner thigh of nude mice. The PP5-specific antisense oligonucleotide, ISIS 15534, or its scrambled control, ISIS 15521, suspended in saline, are administered once daily by intravenous injection at doses ranging from 0.006 to 6.0 mg/kg. Resulting tumors are measured on days 9, 12, 17 and 21 and tumor volumes are calculated.

Example 7

Detection of Protein Phosphatase Expression

PP-specific oligonucleotides are radiolabeled after synthesis by $^{32}P$ labeling at the 5' end with polynucleotide kinase. Sambrook et al., Molecular Cloning. A Laboratory Manual, Cold Spring Harbor Laboratory Press, 1989, Volume 2, pg. 11.31–11.32. Radiolabeled oligonucleotides are contacted with tissue or cell samples suspected of PP expression, such as tumor biopsy samples, under conditions in which specific hybridization can occur, and the sample is washed to remove unbound oligonucleotide. Radioactivity remaining in the sample indicates bound oligonucleotide and is quantitated using a scintillation counter or other routine means.

Analogous assays for fluorescent detection of PP expression use oligonucleotides of the invention which are labeled with fluorescein or other fluorescent tags. Labeled DNA oligonucleotides are synthesized on an automated DNA synthesizer (Applied Biosystems model 380 B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling Va.). Incubation of oligonucleotide and biological sample is carried out as described for radiolabeled oligonucleotides except that instead of a scintillation counter, a fluorimeter or fluorescence microscope is used to detect the fluorescence which indicates PP expression.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

Human PP5 Antisense Oligonucleotides

| Isis # | Sequence (5' → 3') | Target source and site (Genbank #; nucleotide #s) | Target region | Percent Inhibition | SEQ ID NO: |
|---|---|---|---|---|---|
| 14493 | TCGCCCTCCGCCATCGCCAT | x92121; nt 70–89; AUG | AUG | 84% | 1 |
| 14494 | TTCAGAGCTCCATCAGCCGG | x92121; nt 127–146; | coding | 52 | 2 |
| 14495 | GTAGGCCAGGCTGCGGTTGC | u25174; nt 175–194; | coding | 66 | 3 |
| 14496 | CCGCTGTACTCATCCTCAAT | u25174; nt 492–511; | coding | 54 | 4 |
| 14497 | TCCCCACATACTGTAATCTT | u25174; nt 684–703; | coding | 11 | 5 |
| 14498 | GTACTTGGCCTTCACCTCAC | x89416; nt 933–952; | coding | 80 | 6 |
| 14499 | CCAGGTTGTTCTCTTCCAAG | x89416; nt 1225–1244; | coding | 62 | 7 |
| 14500 | AGAGCCCTGGAGGTGGATGT | x89416; nt 1365–1384; | coding | 41 | 8 |
| 14501 | CGCCCCGCCCGTCACCTCAC | x89416; nt 1480–1499; | Stop codon | 42 | 9 |
| 14502 | CCTACCCCCTCTGCAAACCT | x89416; nt 1625–1644; | 3' UTR | 40 | 10 |
| 14503 | GCCCCAGCTGCTCCACCTCC | x89416; nt 1694–1713; | 3' UTR | 27 | 11 |
| 14504 | GGGCCCTATTGCTTGAGTGG | x89416; nt 1810–1829; | 3' UTR | 92 | 12 |
| 14505 | CCCAGCCTAGCCCCACCATG | x89416; nt 1899–1918; | 3' UTR | 23 | 13 |

TABLE 2

| ISIS # | Sequence | Backbone | SEQ ID NO: |
|---|---|---|---|
| 15523 | GGGCCCTATTGCTTGAGTGG | P=S | 12 |
| 15534 | GGGCCCTATTGCTTGAGTGG | P=O/P=S | 12 |
| 15521 | GTGCGATCGTTGCGGTTAGC | P=O/P=S | 14 |

TABLE 3

| ISIS # | Sequence | Backbone | SEQ ID NO: |
|---|---|---|---|
| 14493 | TCGCCCTCCGCCATTCGCCAT | P=O/P=S | 1 |
| 15516 | TCGCCCTCCGCCATCGCCAT | P=S | 1 |
| 15517 | GCTCTACTCCGCCCATGCC | P=O/P=S | 15 |

TABLE 4

Human PP5 Antisense Oligonucleotides

| Isis # | Sequence (5' → 3') | Target source and site (Genbank #; nucleotide #s) | Target region | Percent Inhibition | SEQ ID NO: |
|---|---|---|---|---|---|
| 14375 | CCATGGCCCACCCCCGGCGC | X70218; 123–142 | AUG | 85.6% | 16 |
| 14376 | TGATCTCCGCCATGGCCCAC | X70218; 132–151 | AUG | 81.4 | 17 |
| 14377 | CGGTCCACAAAGTCCCCCAT | X70218; 376–395 | coding | 7.9 | 18 |
| 14378 | GAGGCCCCCGTGCACGCAGA | x70218; 620–639 | coding | 61.9 | 19 |
| 14379 | ACGTCACTGCCAAATAGGTA | X70128; 781–800 | coding | 78.3 | 20 |
| 14380 | TGCCACATTCCCACAGCGGT | X70218; 929–948 | coding | 59.9 | 21 |
| 14381 | GGGAGCAGCCTCAAAGATGA | X70218; 989–1008 | coding | 48.5 | 22 |
| 14383 | GATGGCAGAGTCACAGTGGT | X70218; 1105–1124 | 3' UTR | 63.1 | 23 |
| 14385 | GGGACAGCAGAGCCAGGACA | X70218; 1150–1169 | 3' UTR | 57.8 | 24 |
| 14387 | AACTTCATGGTTCAAGTGGG | X70218; 1247–1266 | 3' UTR | 78.1 | 25 |

TABLE 5

Human PP1γ1 Antisense Oligonucleotides

| Isis # | Sequence (5' → 3') | Target source and site (Genbank #; nucleotide #s) | Target region | Percent Inhibition | SEQ ID NO: |
|---|---|---|---|---|---|
| 14430 | CCATCGCCTTCCCACCGCCG | x74008; 139–158 | AUG | 26% | 26 |
| 14431 | CATATTTTGAGTGGTGCTCC | x74008; 320–339 | coding | 0 | 27 |
| 14432 | TGGCACATTCATGGTTCCCT | x74008; 520–539 | coding | 32 | 28 |
| 14433 | CTCCATGACAGCAGAATATC | x74008; 658–677 | coding | 15 | 29 |
| 14434 | GCAATAATTGGGCGCAGAAA | x74008; 954–973 | coding | 48 | 30 |
| 14435 | GCTTGCTTTGTGATCATACC | x74008; 1097–1116 | coding | 91 | 31 |
| 14436 | GATTCAGAGCACCCTAGGGC | x74008; 1497–1516 | 3' UTR | 73 | 32 |
| 14437 | AGTGATGCTGGCAAGGTTGA | x74008; 1671–1690 | 3' UTR | 37 | 33 |
| 14438 | CCCAAGAAGGCAGCATGTGT | x74008; 1848–1867 | 3' UTR | 16 | 34 |
| 14439 | AATGGACGGGTTCAGGCCTG | x74008; 2004–2023 | 3' UTR | 54 | 35 |
| 14440 | AAAGCATAATCGGTCACTCG | x74008; 2062–2081 | 3' UTR | 31 | 36 |
| 14441 | CACGGTATTGTACACGGTCA | x74008; 2234–2253 | 3' UTR | 55 | 37 |

What is claimed is:

1. An oligonucleotide about 8 to 50 nucleotides in length which is targeted to a nucleic acid encoding a human serine/theonine protein phosphatase and which inhibits protein phosphatase expression, wherein the oligonucleotide is targeted to a translation initiation site, coding region, or 3' untranslated region of mRNA encoding a human serine/theonine protein phosphatase and wherein the oligonucleotide is targeted to mRNA encoding protein phosphatase 5, protein phosphatase 4, or protein phosphatase 1γ1.

2. The oligonucleotide of claim 1 which has at least one modified backbone linkage.

3. The oligonucleotide of claim 1 wherein at least one of the nucleotide units of the oligonucleotide is modified at the 2' position of the sugar moiety.

4. The oligonucleotide of claim 1 in a pharmaceutically acceptable carrier.

5. The oligonucleotide of claim 1 which is a chimeric oligonucleotide.

6. The oligonucleotide of claim 1 which is targeted to mRNA encoding protein phosphatase 5.

7. The oligonucleotide of claim 6 comprising SEQ ID NOs: 1, 2, 3, 4, 6, 7 or 12.

8. The oligonucleotide of claim 1 which is targeted to mRNA encoding protein phosphatase 4.

9. An oligonucleotide of claim 8 comprising SEQ ID NOs: 16, 17, 19, 20, 21, 23, 24, or 25.

10. The oligonucleotide of claim 1 which is targeted to mRNA encoding protein phosphatase 1γ1.

11. The oligonucleotide of claim 10 comprising SEQ ID NO: 31, 32, 35 or 37.

* * * * *

```
                          SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid (iv) ANTI-SENSE: YES (xi) SEQUENCE DESCRIPTION: SEQ ID NO:1:

TCGCCCTCCG CCATCGCCAT                                                       20

(2) INFORMATION FOR SEQ ID NO:2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
```

(iv) ANTI-SENSE: YES (xi) SEQUENCE DESCRIPTION: SEQ ID NO:2:

TTCAGAGCTC CATCAGCCGG                                                          20

(2) INFORMATION FOR SEQ ID NO:3:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iv) ANTI-SENSE: YES (xi) SEQUENCE DESCRIPTION: SEQ ID NO:3:

GTAGGCCAGG CTGCGGTTGC                                                          20

(2) INFORMATION FOR SEQ ID NO:4:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iv) ANTI-SENSE: YES (xi) SEQUENCE DESCRIPTION: SEQ ID NO:4:

CCGCTGTACT CATCCTCAAT                                                          20

(2) INFORMATION FOR SEQ ID NO:5:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iv) ANTI-SENSE: YES (xi) SEQUENCE DESCRIPTION: SEQ ID NO:5:

TCCCCACATA CTGTAATCTT                                                          20

(2) INFORMATION FOR SEQ ID NO:6:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iv) ANTI-SENSE: YES (xi) SEQUENCE DESCRIPTION: SEQ ID NO:6:

GTACTTGGCC TTCACCTCAC                                                          20

(2) INFORMATION FOR SEQ ID NO:7:

(i) SEQUENCE CHARACTERISTICS:
             (A) LENGTH: 20 base pairs

```
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:7:

CCAGGTTGTT CTCTTCCAAG                                                    20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:8:

AGAGCCCTGG AGGTGGATGT                                                    20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:9:

CGCCCCGCCC GTCACCTCAC                                                    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:10:

CCTACCCCCT CTGCAAACCT                                                    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:11:

GCCCCAGCTG CTCCACCTCC                                                    20
```

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:12:

GGGCCCTATT GCTTGAGTGG        20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:13:

CCCAGCCTAG CCCCACCATG        20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:14:

GTGCGATCGT TGCGGTTAGC        20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:15:

GCTCTACTCC GCCCCATGCC        20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:16:

CCATGGCCCA CCCCCGGCGC                                              20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:17:

TGATCTCCGC CATGGCCCAC                                              20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:18:

CGGTCCACAA AGTCCCCCAT                                              20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:19:

GAGGCCCCCG TGCACGCAGA                                              20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:20:

ACGTCACTGC CAAATAGGTA                                              20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: other nucleic acid (iv) ANTI-SENSE: YES (xi) SEQUENCE DESCRIPTION: SEQ ID NO:21:

TGCCACATTC CCACAGCGGT                                                   20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:22:

GGGAGCAGCC TCAAAGATGA                                                   20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:23:

GATGGCAGAG TCACAGTGGT                                                   20

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:24:

GGGACAGCAG AGCCAGGACA                                                   20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:25:

AACTTCATGG TTCAAGTGGG                                                   20

(2) INFORMATION FOR SEQ ID NO:26:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid (iv) ANTI-SENSE: YES (xi) SEQUENCE DESCRIPTION: SEQ ID NO:26:

CCATCGCCTT CCCACCGCCG     20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:27:

CATATTTTGA GTGGTGCTTC     20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:28:

TGGCACATTC ATGGTTCCCT     20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:29:

CTCCATGACA GCAGAATATC     20

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:30:

GCAATAATTG GGCGCAGAAA                                                      20

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:31:

GCTTGCTTTG TGATCATACC                                                      20

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:32:

GATTCAGAGC ACCCTAGGGC                                                      20

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:33:

AGTGATGCTG GCAAGGTTGA                                                      20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:34:

CCCAAGAAGG CAGCATGTGT                                                      20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear -continued

```
    (ii) MOLECULE TYPE: other nucleic acid (iv) ANTI-SENSE: YES (xi) SEQUENCE DESCRIPTION: SEQ ID NO:35:

AATGGACGGG TTCAGGCCTG                                              20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:36:

AAAGCATAAT CGGTCACTCG                                              20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:37:

CACGGTATTG TACACGGTCA                                              20
```